United States Patent [19]

Thyes et al.

[11] 4,271,163

[45] Jun. 2, 1981

[54] NOVEL 3,4-DIAZA-BICYCLO[4.1.0]HEPT-2-EN-5-ONES, THEIR PREPARATION, AND THERAPEUTIC AGENTS CONTAINING THESE COMPOUNDS

[75] Inventors: Marco Thyes, Ludwigshafen; Josef Gries, Wachenheim; Hans D. Lehmann, Hirschberg-Leutershausen; Dieter Lenke, Ludwigshafen; Johannes Kunze, Triftern, all of Fed. Rep. of Germany

[73] Assignee: BASF Aktiengesellschaft, Fed. Rep. of Germany

[21] Appl. No.: 98,854

[22] Filed: Nov. 30, 1979

[30] Foreign Application Priority Data

Dec. 16, 1978 [DE] Fed. Rep. of Germany ....... 2854475

[51] Int. Cl.$^3$ .................... C07D 237/26; A61K 31/50
[52] U.S. Cl. ...................... 424/250; 544/235; 562/460
[58] Field of Search .................. 424/250; 544/235

[56] References Cited

U.S. PATENT DOCUMENTS

| 3,689,652 | 9/1972 | Curran | 424/250 |
| 3,746,712 | 7/1973 | Ross | 544/239 |
| 3,812,256 | 5/1974 | Curran | 424/250 |
| 3,822,260 | 7/1974 | Curran | 544/239 |
| 3,951,176 | 1/1976 | Houlihan | 544/235 |
| 3,975,388 | 8/1976 | Hakim | 424/250 |
| 4,088,762 | 5/1978 | Hakim | 424/250 |

FOREIGN PATENT DOCUMENTS 2150436  4/1972  Fed. Rep. of Germany .
2207517 12/1972  Fed. Rep. of Germany .
2727481  1/1979  Fed. Rep. of Germany .

OTHER PUBLICATIONS

Tetrahedron 30, 501 (1974), Koenig et al.
Maier et al., Chem. Berichte 98, 1965, p. 2438, (1965).
Wermuth et al., Chim. Ther. 6, 109, (1971).

*Primary Examiner*—Mark L. Berch
*Attorney, Agent, or Firm*—Keil & Witherspoon

[57] ABSTRACT

2-Aryl-3,4-diaza-bicyclo-[4.1.0]hept-2-en-5-ones, substituted in the phenyl ring, of the general formula

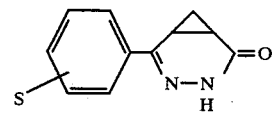

their preparation, and therapeutic agents, containing these compounds, which may be used for the treatment of hypertension or of thrombo-embolic disorders.

17 Claims, No Drawings

NOVEL 3,4-DIAZA-BICYCLO[4.1.0]HEPT-2-EN-5-ONES, THEIR PREPARATION, AND THERAPEUTIC AGENTS CONTAINING THESE COMPOUNDS

The present invention relates to novel 2-aryl-3,4-diaza-bicyclo[4.1.0]hept-2-en-5-ones, processes for their preparation, pharmaceutical formulations containing these compounds, and their use in the prophylaxis and therapy of thrombo-embolic disorders and in cases of hypertension.

German Patent Application P 27 27 481.3 proposes 6-(p-alkanoylaminophenyl)-4,5-dihydro-3(2H)-pyridazinones, which may contain an alkyl radical in the 5-position of the pyridazinone ring, and are halogen-substituted in the alkanoyl radical, for the treatment of thrombo-embolic disorders and hypertension. Other 6-aryl-4,5-dihydro-3(2H)-pyridazinones are stated, for example in German Laid-Open Applications DOS Nos. 2,150,436 and 2,207,517, to have anti-hypertensive properties.

2-Phenyl-3,4-diaza-bicyclo[4.1.0]hept-2-en-5-one is described, for example, by G. Maier in Chem. Ber. 98 (1965), 2438–2445. No information on pharmacological effects of this compound has been disclosed. Further, 2-phenyl-3,4-diaza-bicyclo[4.1.0]hept-2-en-5-one substituted by a morpholinoethyl group at the nitrogen in the 4-position is known (Chim. Ther. 6 (1971), 109–115), and is stated to have analgesic and sedative properties. U.S. Pat. No. 3,931,176 discloses that 2-aryl-3,4-diaza-bicyclo[4.n.0]-2-en-5-ones (n=2, 3 or 4) substituted at the nitrogen in the 4-position possess sedative effects on the central nervous system.

We have found that diaza-bicyclo[4.1.0]heptenones of the general formula I

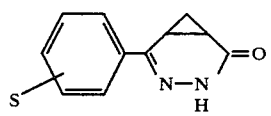

where S is p-alkyl of 1 to 4 carbon atoms, p-cycloalkyl of 4 to 6 carbon atoms in the ring, p-alkoxy of 1 to 3 carbon atoms, p-phenyl, p-halogen, p- or m-amino, m-nitro, p- or m-cyano, p- or m-(pyrrol-1-yl) or p- or m-acylamino of the formula —NHCOR$^1$, where R$^1$ is hydrogen, alkyl of 1 to 8 carbon atoms, which is unsubstituted or substituted by from one to six halogen atoms, cycloalkyl of 3 to 8 carbon atoms in the ring, which is unsubstituted or substituted by from one to four halogen atoms and/or alkyl radicals of 1 to 4 carbon atoms, alkenyl of 2 to 8 carbon atoms or phenyl which is unsubstituted or substituted by alkyl of 1 to 3 carbon atoms, by alkoxy of 1 to 3 carbon atoms or by a halogen atom, possess valuable pharmacological properties.

The diaza-bicyclo[4.1.0]heptenones according to the invention, of the formula I, are described in more detail in the text which follows by giving examples of compounds of the formula II

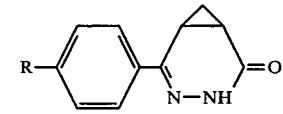

where R is alkyl of 1 to 4 carbon atoms, cycloalkyl of 4 to 6 carbon atoms in the ring, alkoxy of 1 to 3 carbon atoms, phenyl or halogen, of compounds of the formula III

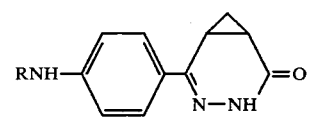

where R is hydrogen or acyl of the formula —COR$^1$, where R$^1$ is hydrogen, alkyl of 1 to 8 carbon atoms, which is unsubstituted or substituted by from one to six halogen atoms, cycloalkyl of 3 to 8 carbon atoms in the ring, which is unsubstituted or substituted by from one to four halogen atoms and/or alkyl radicals of 1 to 4 carbon atoms, alkenyl of 2 to 8 carbon atoms or phenyl which is unsubstituted or substituted as specified for formula I, of compounds of the formula IV

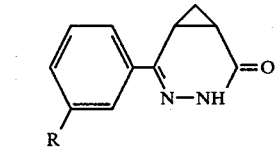

where R is nitro, amino or acylamino of the formula —NHCOR$^1$, where R$^1$ has the meanings given for the same radical —NHCOR$^1$ in formula III, and of compounds of the formula V

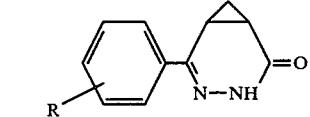

where R is p-cyano, m-cyano, p-(pyrrol-1-yl) or m-(pyrrol-1-yl).

Diaza-bicyclo[4.1.0]heptenones of the formula II:

Examples of straight-chain or branched alkyl R are methyl, ethyl and propyl. Examples of cycloalkyl R are cyclopentyl and cyclohexyl. Examples of alkoxy R are methoxy and ethoxy. Examples of halogen R are chlorine, bromine, iodine and fluorine.

The diaza-bicyclo[4.1.0]heptenones of the formula II may be obtained by cyclizing a cis-2-aroylcyclopropanecarboxylic acid of the formula VII, where R has the meanings given for the radical R of the compounds of the formula II, with hydrazine, in a conventional manner.

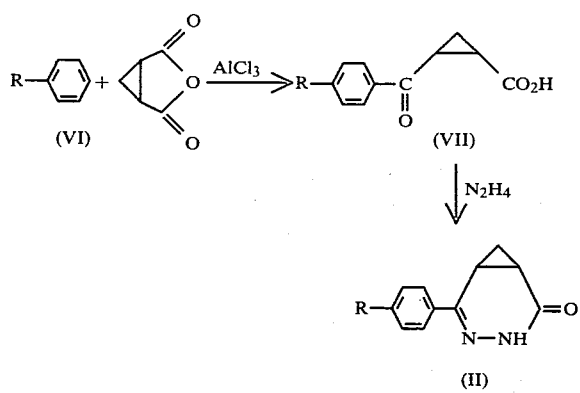

This cyclization reaction with hydrazine, the hydrazine being preferably employed as the hydrate, is advantageously carried out in a solvent which is inert under the reaction conditions, especially a lower alcohol, eg. methanol, ethanol or propanol, a cyclic aliphatic ether, e.g. tetrahydrofuran or dioxane, or a dialkylformamide, e.g. dimethylformamide, at from 60° to 150° C., preferably from 80° to 120° C. As a rule, from 1 to 1.2 moles of hydrazine are employed per mole of compound of the formula VII.

The cis-2-aroylcyclopropanecarboxylic acids of the formula VII can be prepared, as is shown by the equation, by reacting 1,2-cyclopropanedicarboxylic acid anhydride with a benzene derivative of the formula VI, where R has the meanings given for the radical R of the compounds of the formula II, in the presence of aluminum chloride, under the conditions of a Friedel-Crafts reaction. Benzene derivatives of the formula VI, where R is alkoxy, are advantageously reacted in nitrobenzene as the solvent, as is conventionally the case for the Friedel-Crafts acylation of alkoxybenzenes, at from 0° to 60° C. Other substituted benzene derivatives of the formula VI can be acylated at from 0° to 120° C. in a solvent, such as carbon disulfide or nitrobenzene, or, if the benzene derivative employed is liquid, using an excess of benzene derivative as the solvent. The reaction of 1,2-cyclopropanedicarboxylic acid anhydride with a compound of the formula VI, where R is alkyl, cycloalkyl, phenyl or halogen, can also be carried out in a dimethylformamide/aluminum chloride melt at from 50° to 120° C., preferably from 60° to 90° C. In that case, as a rule about 10 moles of aluminum chloride and about 2.5 moles of dimethylformamide are used per mole of 1,2-cyclopropanedicarboxylic acid anhydride or per mole of benzene derivative VI.

The following are examples of compounds, according to the invention, obtained by the process described: 2-(p-tolyl)-3,4-diaza-bicyclo[4.1.0]hept-2-en-5-one, 2-(p-ethylphenyl)-3,4-diaza-bicyclo[4.1.0]hept-2-en-5-one, 2-(p-cyclopentylphenyl)-3,4-diaza-bicyclo[4.1.0]hept-2-en-5-one, 2-(p-cyclohexylphenyl)-3,4-diaza-bicyclo[4.1.0]hept-2-en-5-one, 2-(p-methoxyphenyl)-3,4-diaza-bicyclo-[4.1.0]hept-2-en-5-one, 2-(p-ethoxyphenyl)-3,4-diaza-bicyclo[4.1.0]hept-2-en-5-one, 2-(p-biphenylyl)-3,4-diaza-bicyclo[4.1.0]hept-2-en-5-one, 2-(p-chlorophenyl)-3,4-diaza-bicyclo[4.1.0]hept-2-en-5-one, 2-(p-bromophenyl)-3,4-diaza-bicyclo[4.1.0]hept-2-en-5-one and 2-(p-fluorophenyl)-3,4-diaza-bicyclo[4.1.0]hept-2-en-5-one. Diaza-bicyclo[4.1.0]heptenones of the formula III:

Where the radical $R^1$ in the acyl group —$COR^1$ is straight or branched alkyl of 1 to 8 carbon atoms, examples thereof are methyl, ethyl, propyl, isopropyl, butyl, isobutyl, sec.-butyl, tert.-butyl and n-pentyl.

Where the radical $R^1$ in the acyl group —$COR^1$ is straight-chain or branched alkyl of 1 to 8 carbon atoms substituted by halogen, eg. chlorine, bromine, fluorine or iodine, examples thereof are chloromethyl, bromomethyl, fluoromethyl, iodomethyl, 1-chloroethyl, 1-bromoethyl, 1-fluoroethyl, 1-iodoethyl, 2-chloroethyl, 2-bromoethyl, 2-fluoroethyl, 2-iodoethyl, 1-chloropropyl, 1-bromopropyl, 1-fluoropropyl, 1-iodopropyl, 2-chloropropyl, 2-bromopropyl, 3-chloropropyl, 3-bromopropyl, 3-fluoropropyl, 1-chloroisopropyl, 1-bromoisopropyl, 1-iodoisopropyl, 2-chloroisopropyl, 2-bromoisopropyl, 1-chlorobutyl, 1-bromobutyl, 1-fluorobutyl, 4-chlorobutyl, 4-bromobutyl, 1-chloroisobutyl, 1-bromoisobutyl, 2-chloroisobutyl, 1-chloro-sec.-butyl, 1-bromo-sec.-butyl, 3-chloro-sec.-butyl, chloro-tert.-butyl, bromo-tert.butyl, 1-chloropentyl, 1-bromopentyl, 1-ethyl-1-chloropropyl, 1-ethyl-1-bromopropyl, dichloromethyl, difluoromethyl, 1,1-dichloroethyl, 1,2-dichloroethyl, 1,2-dibromoethyl, 2,2-dichloroethyl, 1,1-dichloropropyl, 1,2-dichloropropyl, 1,2-dibromopropyl, 1,3-dichloropropyl, 2,3-dibromopropyl, 1,2-dichloroisopropyl, 1,4-dichlorobutyl, 1,2-dibromoisobutyl, 1,1-bis-chloromethyl-ethyl, trichloromethyl, trifluoromethyl, chlorodifluoromethyl and 1,1,2,2-tetrafluoroethyl.

The preferred alkyl radicals $R^1$ are of 1 to 4 carbon atoms and may be unsubstituted or substituted, preferably by from one to three halogen atoms, in particular fluorine, chlorine or bromine.

Where $R^1$ in the acyl group —$COR^1$ is unsubstituted or substituted cycloalkyl of 3 to 8 carbon atoms in the ring, examples are cyclopropyl, 1-methylcyclopropyl, 2-methylcyclopropyl, 2,2-dimethylcyclopropyl, 2,2,3,3-tetramethylcyclopropyl, 1-chlorocyclopropyl, 2-bromocyclopropyl, 2,2-dichlorocyclopropyl, 2,2-dibromocyclopropyl, 2,2-dichloro-1-methylcyclopropyl, cyclobutyl, 1-methylcyclobutyl, 2-methylcyclobutyl, 3-methylcyclobutyl, 3,3-dimethylcyclobutyl, 1-propylcyclobutyl, 3-tertiary butylcyclobutyl, 1-chlorocyclobutyl, 2-chlorocyclobutyl, 3-chlorocyclobutyl, 1-bromocyclobutyl, 2,2,3,3-tetrafluorocyclobutyl, 1-bromo-3,3-dimethylcyclobutyl, cyclopentyl, 1-methylcyclopentyl, 2,5-dimethylcyclopentyl, 1-chlorocyclopentyl, 3,4-dichlorocyclopentyl, cyclohexyl and 1-methylcyclohexyl.

Preferred cycloalkyl radicals are those of 3 to 5 carbon atoms in the ring, which are unsubstituted or monosubstituted, disubstituted or trisubstituted by halogen and/or methyl.

Where $R^1$ is alkenyl of 2 to 8 carbon atoms, examples are vinyl, propenyl, isopropenyl, allyl, but-1-enyl, but-2-enyl, but-3-enyl, 2-methyl-prop-1-enyl and pent-1-enyl.

The compounds of the formula III, where R is acyl of the formula —$COR^1$, $R^1$ having the above meanings (compounds IIIa), are obtained by cyclizing a cis-2-(p-acylaminobenzoyl)-cyclopropanecarboxylic acid of the formula IX, where $R^1$ has the meanings given for the same radical in formula IIIa, with hydrazine in a conventional manner.

The starting compounds of the formula IX are obtained by reacting an anilide of the formula VIII, where $R^1$ has the meanings given for the same radical in formula IIIa, with 1,2-cyclopropanedicarboxylic acid anhydride in the presence of aluminum chloride, under the conditions of a Friedel-Crafts acylation.

where $R^1$ and X have the above meanings, and cyclizing the resulting acylamino compound of the formula IX

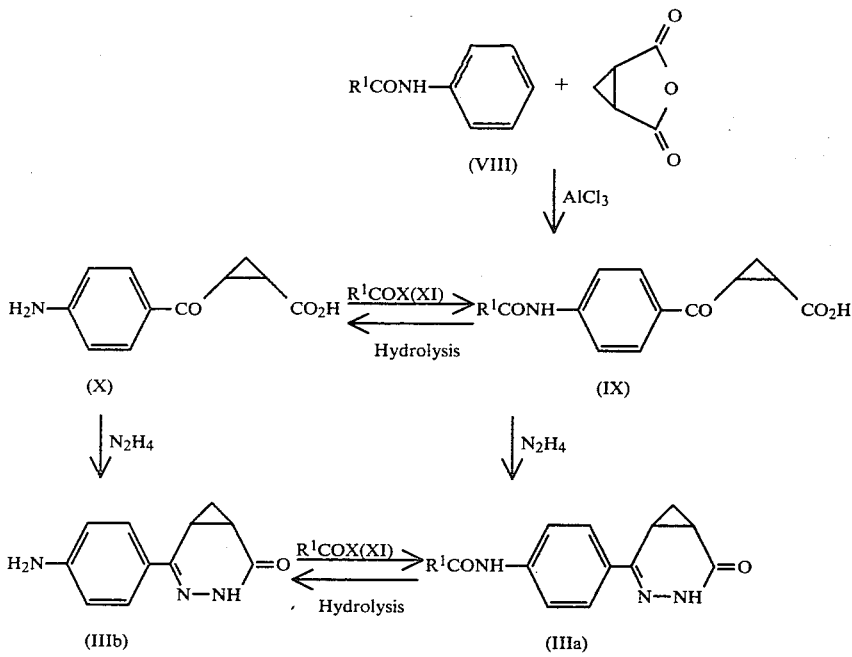

The compound of the formula III, where R is hydrogen (compound III b), can be prepared by hydrolyzing a diaza-bicyclo[4.1.0]heptenone of the formula III a, for example 2-(p-acetylaminophenyl)-3,4-diaza-bicyclo-[4.1.0]hept-2-en-5-one (III a: $R^1$=—$CH_3$). This hydrolysis is carried out by conventional methods, for example with aqueous sodium hydroxide in the presence of a lower alcohol, e.g. methanol or ethanol, as the solvent, at the reflux temperature.

The diaza-bicyclo[4.1.0]heptenone of the formula III b can also be obtained by cyclizing the aminoacid of the formula X with hydrazine in a conventional manner. The compound X is obtained by hydrolyzing a cis-2-(p-acylaminobenzoyl)-cyclopropanecarboxylic acid of the formula IX, for example cis-2-(p-acetylaminobenzoyl)-cyclopropanecarboxylic acid (IX: $R^1$=$CH_3$), by conventional methods, for example by means of aqueous hydrochloric acid.

The diaza-bicyclo[4.1.0]heptenones of the formula III a can also be prepared by reacting the amino compound III b with an acylating agent of the formula XI $R^1COX$                        (XI)

where $R^1$ has the meanings given for the same radical in formula III a and X is chlorine, OH, lower alkoxy or a radical of the formula $OCOR^1$. In accordance with the meanings given for X, acylating agents are the corresponding carboxylic acid chlorides, carboxylic acids, carboxylic acid esters, especially methyl esters and ethyl esters, and carboxylic acid anhydrides.

According to a further method of preparation, the compounds of the formula III a are obtained by acylating the aminoacid of the formula X with an acylating agent of the formula XI $R^1COX$                        (XI)

with hydrazine in a conventional manner.

The compounds of the formula III a, where $R^1$ is halogen-substituted alkyl or cycloalkyl, or is alkenyl, are preferably prepared by acylating the aminophenyl-diaza-bicyclo[4.1.0]heptenone of the formula III b.

The Friedel-Crafts acylation of an anilide of the formula VIII with 1,2-cyclopropanedicarboxylic acid anhydride, to give a cyclopropanecarboxylic acid of the formula IX, can be carried out in a solvent, for example carbon disulfide, at from 0° to 60° C. It can also be carried out in a dimethylformamide/aluminum chloride melt at from 50° to 120° C., preferably from 60° to 90° C. In that case it is advantageous to use about 10 moles of aluminum chloride and about 2.5 moles of dimethylformamide per mole of 1,2-cyclopropanedicarboxylic acid anhydride or per mole of anilide of the formula VIII.

The acylation of the diaza-bicyclo[4.1.0]heptenone III b or of the aminoacid X with an acylating agent of the formula XI to give a diaza-bicyclo[4.1.0]heptenone III a or a cis-2-(p-acylaminobenzoyl)-cyclopropanecarboxylic acid of the formula IX is carried out under conventional conditions, as a rule using not less than an equimolar amount of the acylating agent, advantageously in the presence of a solvent, and in the presence or absence of an auxiliary base, at from 0° to 160° C., if appropriate at the boiling point of the reaction mixture, and if appropriate under superatmospheric pressure. Suitable solvents are those which are inert under the reaction conditions, such as aromatic hydrocarbons, e.g. toluene or xylene, cyclic aliphatic ethers, e.g. tetrahydrofuran or dioxane, or dialkylformamides, e.g. dimethylformamide. Auxiliary bases used as acid acceptors are advantageously inorganic bases, e.g. sodium carbonate, potassium carbonate, sodium bicarbonate or potassium bicarbonate, or tertiary organic amines, e.g. triethylamine.

The cyclization of a cis-2-(p-acylaminobenzoyl)-cyclopropanecarboxylic acid of the formula IX or of the animoacid of the formula X with hydrazine, the latter being preferably employed as the hydrate, to give a diaza-bicyclo[4.1.0]heptenone of the formula III a or to give the amino compound III b, is carried out under the conditions described above for the reaction of the compounds of the formula VII with hydrazine.

Examples of compounds according to the invention obtained using the above processes are the following: 2-(p-aminophenyl)-3,4-diaza-bicyclo[4.1.0]hept-2-en-5-one, 2-(p-formylaminophenyl)-3,4-diaza-bicyclo[4.1.0]-hept-2-en-5-one, 2-(p-acetylaminophenyl)-3,4-diaza-bicyclo[4.1.0]hept-2-en-5-one, 2-(p-propionylaminophenyl)-3,4-diaza-bicyclo[4.1.0]hept-2-en-5-one, 2-(p-butyrylaminophenyl)-3,4-diaza-bicyclo[4.1.0]hept-2-en-5-one, 2-(p-isobutyrylaminophenyl)-3,4-diaza-bicyclo[4.1.0]-hept-2-en-5-one, 2-(p-valerylaminophenyl)-3,4-diaza-bicyclo[4.1.0]hept-2-en-5-one, 2-(p-isovalerylaminophenyl)-3,4-diaza-bicyclo[4.1.0]hept-2-en-5-one, 2-p-(2-methylbutyrylamino)-phenyl-3,4-diaza-bicyclo[4.1.0]hept-2-en-5-one, 2-(p-pivaloylaminophenyl)-3,4-diaza-bicyclo[4.1.0]hept-2-en-5-one, 2-(p-chloroacetylaminophenyl)-3,4-diaza-bicyclo[4.1.0]hept-2-en-5-one, 2-(p-bromoacetylaminophenyl)-3,4-diaza-bicyclo[4.1.0]hept-2-en-5-one, 2-(p-fluoroacetylaminophenyl)-3,4-diaza-bicyclo[4.1.0]hept-2-en-5-one, 2-(p-iodoacetylaminophenyl)-3,4-diazabicyclo[4.1.0]hept-2-en-5-one, 2-[p-(2-chloropropionylamino)-phenyl]-3,4-diaza-bicyclo[4.1.0]hept-2-en-5-one, 2-[p-(2-bromopropionylamino)-phenyl]-3,4-diaza-bicyclo[4.1.0]hept-2-en-5-one, 2-[p-(3-chloropropionylamino)-phenyl]-3,4-diaza-bicyclo[4.1.0]hept-2-en-5-one, 2-[p-(3-bromopropionylamino)-phenyl]-3,4-diaza-bicyclo[4.1.0]hept-2-en-5-one, 2-[p-(2-chlorobutyrylamino)-phenyl]-3,4-diaza-bicyclo[4.1.0]hept-2-en-5-one, 2-[p-(2-bromobutyrylamino)-phenyl]-3,4-diaza-bicyclo[4.1.0]hept-2-en-5-one, 2-[p-(4-chlorobutyrylamino)-phenyl]-3,4-diaza-bicyclo[4.1.0]hept-2-en-5-one, 2-[p-(2-chloroisobutyrylamino)-phenyl]-3,4-diaza-bicyclo-[4.1.0]hept-2-en-5-one, 2-[p-(2-bromovalerylamino)-phenyl]-3,4-diaza-bicyclo[4.1.0]hept-2-en-5-one, 2-(p-chloropivaloylaminophenyl)-3,4-diaza-bicyclo[4.1.0]hept-2-en-5-one, 2-(p-bromopivaloylaminophenyl)-3,4-diaza-bicyclo[4.1.0]hept-2-en-5-one, 2-[p-(2-ethyl-2-bromobutyrylamino)-phenyl]-3,4-diaza-bicyclo[4.1.0]hept-2-en-5-one, 2-(p-dichloroacetylaminophenyl)-3,4-diaza-bicyclo[4.1.0]hept-2-en-5-one, 2-(p-difluoroacetylaminophenyl)-3,4-diaza-bicyclo[4.1.0]hept-2-en-5-one, 2-[p-(2,2-dichloropropionylamino)-phenyl]-3,4-diaza-bicyclo[4.1.0]-hept-2-en-5-one, 2-[p-(2,3-dichloropropionylamino)-phenyl]-3,4-diaza-bicyclo[4.1.0]hept-2-en-5-one, 2-[p-(2,2-dichlorobutyrylamino)-phenyl]-3,4-diaza-bicyclo[4.1.0]hept-2-en-5-one, 2-[p-(2,4-dichlorobutyrylamino)-phenyl]-3,4-diaza-bicyclo[4.1.0]hept-2-en-5-one, 2-(p-trichloroacetylaminophenyl)-3,4-diaza-bicyclo[4.1.0]hept-2-en-5-one, 2-(p-trifluoroacetylaminophenyl)-3,4-diaza-bicyclo[4.1.0]hept-2-en-5-one, 2-(p-chlorodifluoroacetylaminophenyl)-3,4-diaza-bicyclo[4.1.0]hept-2-en-5-one, 2-(p-cyclopropylcarbonylaminophenyl)-3,4-diaza-bicyclo-[4.1.0]hept-2-en-5-one, 2-[p-(1-methylcyclopropylcarbonylamino)-phenyl]-3,4-diaza-bicyclo[4.1.0]hept-2-en-5-one, 2-[p-(2-methylcyclopropylcarbonylamino)-phenyl]-3,4-diaza-bicyclo[4.1.0]hept-2-en-5-one, 2-[p-(2,2-dimethylcyclopropylcarbonylamino)-phenyl]-3,4-diaza-bicyclo-[4.1.0]hept-2-en-5-one, 2-[p-(1chlorocyclopropylcarbonylamino)-phenyl]-3,4-diaza-bicyclo[4.1.0]hept-2-en-5-one, 2-[p-(2-bromocyclopropylcarbonylamino)-phenyl]-3,4-diaza-bicyclo[4.1.0]hept-2-en-5-one, 2-[p-(2,2-dichlorocyclopropylcarbonylamino)-phenyl]-3,4-diaza-bicyclo[4.1.0]-hept-2-en-5-one, 2-[p-(2,2-dichloro-1-methylcyclopropylcarbonylamino)-phenyl]-3,4-diaza-bicyclo[4.1.0]hept-2-en-5-one, 2-(pcyclobutylcarbonylaminophenyl)-3,4-diaza-bicyclo[4.1.0]hept-2-en-5-one, 2-[p-(2-methylcyclobutylcarbonylamino)-phenyl]-3,4-diaza-bicyclo[4.1.0]hept-2-en-5-one, 2-[p-(1-chlorocyclobutylcarbonylamino)-phenyl]-3,4-diaza-bicyclo[4.1.0]hept-2-en-5-one, 2-[p-(2-chlorocyclobutylcarbonylamino)-phenyl]-3,4-diaza-bicyclo-[4.1.0]hept-2-en-5-one, 2-[p-(3-chlorocyclobutylcarbonylamino)-phenyl]-3,4-diaza-bicyclo[4.1.0]hept-2-en-5-one, 2-(p-cyclopentylcarbonylaminophenyl)-3,4-diaza-bicyclo[4.1.0]hept-2-en-5-one, 2-(p-cyclohexylcarbonylaminophenyl)-3,4-diaza-bicyclo[4.1.0]hept-2-en-5-one, 2-(p-acryloylaminophenyl)-3,4-diaza-bicyclo[4.1.0]hept-2-en-5-one, 2-(p-crotonoylaminophenyl)-3,4-diaza-bicyclo[4.1.0]-hept-2-en-5-one, 2-(p-methacryloylaminophenyl)-3,4-diaza-bicyclo[4.1.0]hept-2-en-5-one, 2-[p-(but-3-enoylamino)-phenyl]-3,4-diaza-bicyclo[4.1.0]hept-2-en-5-one and 2-(p-benzoylaminophenyl)-3,4-diaza-bicyclo[4.1.0]hept-2-en-5-one.

Diaza-bicyclo[4.1.0]heptenones of the formula IV

Where the radical $R^1$ in the acylamino group —NHCOR$^1$ is alkyl of 1 to 8 carbon atoms which is unsubstituted or substituted by halogen, e.g. chlorine, bromine, fluorine or iodine, or is unsubstituted or substituted cycloalkyl of 3 to 8 carbon atoms in the ring, or is alkenyl of 2 to 8 carbon atoms, examples of $R^1$ are the same as those given in connection with the p-acylamino group —NHCOR$^1$ of the compounds of the formula III.

The diaza-bicyclo[4.1.0]heptenone of the formula IV, where R is nitro (compound IV a) can be prepared by reacting the compound of the formula XIII with hydrazine in a conventional manner.

The cyclopropanecarboxylic acid of the formula XIII is obtained by nitrating the cis-2-benzoylcyclopropanecarboxylic acid of the formula XII, for example with a mixture of concentrated nitric acid and concentrated sulfuric acid. Compound XII is known. Its preparation is described, for example, by G. Maier, Chem. Ber. 98 (1965), 2438–2445 and by C. G. Wermuth, G. Leclerc and J. Schreiber, Chim. Ther., 6 (1971), 109–115.

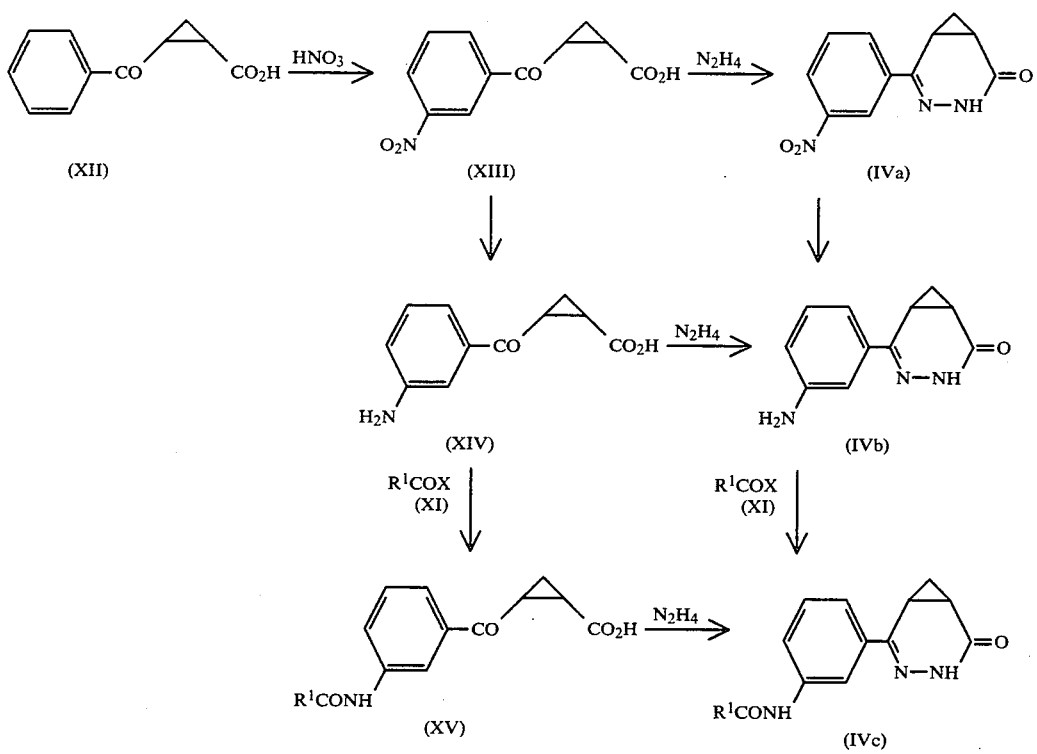

The compound of the formula IV, where R is amino (compound IV b) is obtained by cyclizing the aminoacid of the formula XIV with hydrazine in a conventional manner.

Compound XIV may be obtained by reducing the nitro group of the compound XIII to an amino group with iron and acetic acid. This Bechamp reduction is carried out in a conventional manner, for example in the presence of water as a solvent, and with heating, preferably at the boiling point of the reaction mixture. It is advantageous to pre-etch the iron by heating it with the acetic acid before adding the nitro compound.

According to another method of preparation, the compound IV b may be obtained by reducing the nitro group of the diaza-bicyclo[4.1.0]heptenone IV a to an amino group. This conversion may be carried out by methods conventionally used for reducing nitro groups attached to aromatic nuclei. Examples of such methods are reductions with hydrogen or hydrazine in the presence of a metal catalyst, eg. palladium or Raney nickel, or reduction with an unsaturated hydroaromatic compound, preferably cyclohexane, in the presence of a palladium catalyst. Other possible methods are reductions using a metal-acid combination, for example tin, zinc or iron with hydrochloric acid, sulfuric acid or acetic acid.

The reduction of the nitro group of IV a with hydrogen in the presence of a metal catalyst is carried out in a solvent which is inert under the reaction conditions, especially a lower alcohol, eg. methanol, ethanol or propanol, a cyclic aliphatic ether, eg. tetrahydrofuran or dioxane, a glycol ether, eg. glycol dimethyl ether, or a dialkylformamide, eg. dimethylformamide, at room temperature or an elevated temperature, advantageously at from 20° to 100° C., if appropriate under superatmospheric pressure. The preferred catalyst is palladium on charcoal.

The reduction of the nitro group of IV a with hydrazine in the presence of a palladium catalyst or Raney nickel catalyst is carried out in a solvent which is inert under the reaction conditions, for example a lower alcohol, eg. methanol, ethanol, propanol or butanol. As a rule, from 1.5 to 4 moles of hydrazine, preferably in the form of the hydrate, are employed per mole of the compound IV a. The reduction is carried out at room temperature and is preferably completed by heating at 50°–120° C.

The reduction of the nitro group of IV a with cyclohexane and a palladium catalyst is advantageously carried out in a solvent which is inert under the reaction conditions, especially a lower alcohol, eg. methanol, ethanol, propanol or butanol, or a cyclic aliphatic ether, eg. tetrahydrofuran or dioxane, at from 50° to 120° C., preferably at the boiling point of the reaction mixture, and advantageously using a large excess of cyclohexene. As a rule, palladium on charcoal is used as the catalyst.

Amongst the reductions using a metal-acid combination, the Bechamp reduction with iron and acetic acid is particularly important. It can for example be carried out in the presence of a lower alcohol, eg. methanol, ethanol, propanol or butanol, as the solvent, at from 50° to 120° C. It is advantageous to pre-etch the iron by heating it with the acetic acid before adding the nitro compound.

The compounds of the formula IV, where R is acylamino of the formula —NHCOR$^1$, R$^1$ having the above meanings (compounds IV c), can be prepared by reacting the amino compound of the formula IV b with an acylating agent of the formula XI

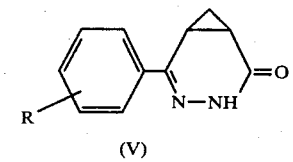

where $R^1$ has the same meanings as the radical $R^1$ in the compounds IV c and X is chlorine, OH, lower alkoxy or $OCOR^1$.

In accordance with the meanings given for X, advantageous acylating agents are the same derivatives as those used, for example, for the acylation, described above, of the diaza-bicyclo[4.1.0]heptenone III b to give a compound of the formula III a.

It is also possible to arrive at a compound of the formula IV c by acylating the aminoacid XIV with an acylating agent of the formula XI $R^1COX$ (XI)

where $R^1$ and X have the above meanings, and cyclizing the resulting acylamino compound of the formula XV with hydrazine.

The acylation of the diaza-bicyclo[4.1.0]heptenone IV b or of the aminoacid XIV with an acylating agent of the formula XI to give a compound of the formula IV c or XV is carried out under the above conditions as described for the acylation of the corresponding p-compounds III b and X with an acylating agent of the formula XI.

The cyclization of the cis-2-aroylcyclopropanecarboxylic acids XIII, XIV and XV with hydrazine, the latter being preferably employed as the hydrate, to give the diaza-bicyclo[4.1.0]heptenones IV a, IV b and IV c, is carried out under the conditions described above for the reaction of the compounds of the formula VII with hydrazine.

Compounds of the formula IV c, where $R^1$ is alkyl or cycloalkyl substituted by halogen, or is alkenyl, are preferably prepared by acylating the aminophenyl-diaza-bicyclo[4.1.0]heptenone IV b.

Examples of compounds according to the invention which are obtainable by the processes mentioned are: 2-(m-nitrophenyl)-3,4-diaza-bicyclo[4.1.0]hept-2-en-5-one, 2-(m-aminophenyl)-3,4-diaza-bicyclo[4.1.0]hept-2-en-5-one, 2-(m-formylaminophenyl)-3,4-diaza-bicyclo[4.1.0]hept-2-en-5-one, 2-(m-acetylaminophenyl)-3,4-diaza-bicyclo[4.1.0]hept-2-en-5-one, 2-(m-propionylaminophenyl)-3,4-diaza-bicyclo[4.1.0]hept-2-en-5-one, 2-(m-chloroacetylaminophenyl)-3,4-diaza-bicyclo[4.1.0]hept-2-en-5-one, 2-[m-(3-chloropropionylamino)-phenyl]-3,4-diaza-bicyclo[4.1.0]hept-2-en-5-one, 2-(m-dichloroacetylaminophenyl)-3,4-diaza-bicyclo[4.1.0]hept-2-en-5-one, 2-(m-cyclopropylcarbonylaminophenyl)-3,4-diaza-bicyclo[4.1.0]hept-2-en-5-one and 2-(m-acryloylaminophenyl)-3,4-diaza-bicyclo[4.1.0]hept-2-en-5-one.

Diaza-bicyclo[4.1.0]heptenones of the formula V

The diaza-bicyclo[4.1.0]heptenones of the formula V can be prepared by cyclizing a compound of the formula XVI, where R has the meanings given above for the radical R of the compounds of the formula V with hydrazine in a conventional manner.

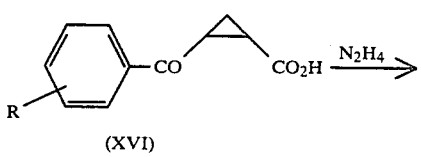

(XVI)

(V)

The cyclization reaction of hydrazine, the latter being preferably employed as the hydrate, is carried out under the conditions given above for the reaction of the compounds of the formula VII with hydrazine.

The cis-2-aroylcyclopropanecarboxylic acids of the formula XVI, where R is p- or m-cyano, are obtained by diazotizing the aminoacids X or XIV in a conventional manner and then replacing the diazonium group by a cyano radical using the Sandmeyer method.

To prepare the cis-2-aroylcyclopropanecarboxylic acids of the formula XVI, where R is p- or m-(pyrrol-1-yl), the aminoacids X or XIV are reacted with a 2,5-dialkoxytetrahydrofuran of the formula XVII

(XVII)

where R is alkyl of up to three carbon atoms, for example methyl or ethyl, in a conventional manner.

According to a further method of preparation, the compounds of the formula V, where R is p- or m-cyano, can be prepared by diazotizing the aminophenyl-diaza-bicyclo[4.1.0]heptenones III b or IV b and then replacing the diazonium group by a cyano group.

The compounds of the formula V, where R is p- or m-(pyrrol-1-yl), may also be obtained by reacting the aminophenyl-diaza-bicyclo[4.1.0]heptenones III b or IV b with a dialkoxytetrahydrofuran of the formula XVII

(XVII)

where R has the above meanings.

The diazotization of the amino compounds X, XIV, III b and IV b is carried out in an aqueous medium at from 0° to 5° C. by treatment with an amount of an alkali metal nitrite, preferably sodium nitrite, which is equivalent to the amino compound employed, in the presence of a mineral acid, eg. hydrochloric acid or sulfuric acid. From 2.5 to 10 moles of the mineral acid are used per mole of amine and of alkali metal nitrite. To replace the diazonium group by cyano, the diazonium salt solution obtained is neutralized with a base, eg. sodium carbonate, and then added, at 0°–5° C., to an aqueous solution, covered with a layer of toluene, of copper-(I) cyanide and potassium cyanide. The reaction is terminated by stirring for several hours at room temperature, with or without subsequent brief heating at about 50° C.

The reaction of the aminoacids X and XIV and of the aminophenyl-diaza-bicyclo[4.1.0]heptenones III b and IV b with a dialkoxytetrahydrofuran of the formula XVII is carried out in the presence of an acid and advantageously in the presence of a suitable solvent at from 60° to 140° C., preferably from 80° to 120° C. For example, it may be carried out in an aromatic hydrocarbon, eg. toluene, in the presence of a catalytic amount of a sulfonic acid, eg. benzenesulfonic acid or p-toluenesulfonic acid, or in acetic acid.

It should be noted that the compounds according to the invention, of the formula I, possess asymmetric carbon atoms in positions 1 and 6 of the 3,4-diaza-bicyclo[4.1.0]hept-2-en-5-one ring and are obtained as racemates. The present invention also encompasses the enantiomers, which can be separated, using conventional methods, by means of an optically active acid, eg. dibenzoyltartaric acid or camphor-10-sulfonic acid. If desired, the separation may be carried out at an intermediate stage of the preparative process.

The 2-aryl-3,4-diaza-bicyclo[4.1.0]heptenones according to the invention, of the formula I, are distinguished by a powerful thrombocyte aggregation-inhibiting action and by a powerful blood pressure lowering action. Accordingly, they may be used as anti-hypertensive agents, and for the prophylaxis and therapy of thrombo-embolic disorders.

Accordingly, the present invention also relates to therapeutic agents or formulations which in addition to conventional pharmaceutical carriers and diluents contain a compound of the formula I as the active compound, as well as to the use of these compounds for therapeutic purposes in the treatment of hypertension and of thrombo-embolic disorders.

The following methods were used to investigate the pharmacodynamic properties of the products according to the invention:

1. Inhibition of the collagen-induced aggregation of human thrombocytes in vitro.

Thrombocyte-rich plasma is obtained by centrifuging venous citrate blood (300 g, 10 minutes duration at 4° C.). The photometric measurement of the thrombocyte aggregation is carried out with addition of $MgCl_2$ (final concentration 10 millimoles/l) and of collagen Stago (final concentration 0.02 mg/ml) in a Born Mk 3 aggregometer. The maximum extinction change/sec is used as a measure of the aggregation.

The aggregation-inhibiting activity of the substances is tested after an incubation time of 10 minutes.

The EC 50% is taken to be the concentration causing 50% inhibition of aggregation.

2. Inhibition of the collagen-induced aggregation of rat thrombocytes ex vivo.

The substances are administered orally to groups of 10-15 male Sprague-Dawley rat weighing 200-250 g. 1-4 hours after administration, blood is taken under ether narcosis and thrombocyte-rich plasma is obtained by centrifuging. The aggregation after addition of collagen is measured as indicated above. The ED 33% is determined as the dose which inhibits the collagen-induced thrombocyte aggregation by 33%.

3. Anti-hypertensive effect on narcotized rats.

To test the anti-hypertensive effect, the substances are administered intraperitoneally to groups of 3-5 male Sprague-Dawley rats weighing 240-280 g, under urethane narcosis (1.78 mg/kg given intraperitoneally).

The measurement of the blood pressure in the carotid artery is carried out by means of Statham transducers. The ED 20% is determined as the dose which lowers the mean carotid blood pressure by 20%.

4. Anti-hypertensive effect on spontaneously hypertonic rats.

The substances are administered orally to groups of 4-8 male spontaneously hypertonic Okamoto rats weighing 270-340 g. Before, and 2 hours after, the administration, the systolic blood pressure is measured non-surgically by means of piezo-electric crystal sensors.

The ED 20% is determined as the dose which lowers the systolic pressure by 20%, taking into account the values found with untreated control animals.

The effective doses or effective concentrations were calculated from the linear relationships between the logarithm of the dose or concentration and the logarithm of the effect, by means of regression analysis.

Acetylsalicylic acid was used as the reference substance for the inhibition of thrombocyte aggregation and dihydralazine for the anti-hypertensive effect.

The results in Table 1 show that the compounds according to the invention produce an exceptionally powerful inhibition of the collagen-induced aggregation of human thrombocytes. The effect is from 73 to 3,530 times more powerful than that of the conventional aggregation-inhibiting drug acetylsalicylic acid.

In addition to the inhibition of thrombocyte aggregation, the novel compounds produce an anti-hypertensive effect of varying intensity. In rats, individual compounds prove substantially more powerful than the conventional anti-hypertensive agent dihydralazine. Thus, the compounds of Examples No. 13 and No. 11 are respectively 7.25 and 2.52 times as active as dihydralazine, as may be seen from Table 2.

A fact of particular importance as regards the pharmacotherapeutic use of the compounds is that the inhibition of thrombocyte aggregation is very pronounced also after oral administration in vivo and far surpasses the effect of acetylsalicylic acid, as may be seen from Table 3 (Examples 7, 11, 13 and 20).

Similarly, an anti-hypertensive effect is demonstrable in spontaneously hypertonic rats after oral administration of the compounds of Examples 7, 11, 13 and 20.

TABLE 1

| Inhibition of collagen-induced thrombocyte aggregation in vitro | | |
|---|---|---|
| Compound | Inhibition of aggregation[1] | |
| Example No. | EC 50% | R.A.[2] |
| 7 | 0.14 | 3530 |
| 10 | 6.81 | 73 |
| 11 | 0.28 | 1760 |
| 12 | 0.95 | 518 |
| 13 | 5.57 | 89 |
| 14 | 0.38 | 1310 |
| 15 | 1.87 | 264 |
| 16 | 4.88 | 101 |
| 18 | 3.99 | 124 |
| 19 | 3.52 | 140 |
| 20 | 0.99 | 499 |
| 21 | 2.27 | 218 |
| 22 | 3.47 | 142 |
| 23 | 2.99 | 165 |
| 24 | 3.20 | 154 |
| 25 | 1.80 | 274 |
| 26 | 1.91 | 259 |
| 27 | 1.42 | 348 |
| 28 | 5.09 | 97 |
| 29 | 2.12 | 233 |
| 30 | 6.01 | 82 |
| Acetylsalicylic acid | 494 | 1.00 |

[1]Human thrombocytes in vitro. EC 50% (mg/l) = concentration which inhibits the collagen-induced aggregation by 50%.
[2]R.A. = relative activity; acetysalicylic acid = 1.00

TABLE 2

| Compound Example No. | Anti-hypertensive effect | |
|---|---|---|
| | Reduction in blood pressure[1] | |
| | ED 20% | R.A.[2] |
| 7 | 0.193 | 1.75 |
| 10 | 0.253 | 1.33 |
| 11 | 0.134 | 2.52 |
| 12 | 0.299 | 1.13 |
| 13 | 0.0465 | 7.25 |
| 14 | 0.298 | 1.13 |
| 15 | 1.88 | 0.18 |
| 16 | 0.402 | 0.84 |
| 18 | 0.900 | 0.37 |
| 19 | 0.688 | 0.49 |
| 20 | 0.278 | 1.21 |
| 21 | 6.81 | 0.05 |
| 22 | 2.96 | 0.11 |
| 23 | 1.50 | 0.23 |
| 24 | 10.0 | 0.03 |
| 25 | 0.649 | 0.52 |
| 26 | 0.786 | 0.43 |
| 27 | 0.398 | 0.85 |
| 28 | 0.415 | 0.81 |
| 29 | 1.71 | 0.20 |
| 30 | >10.0 | <0.03 |
| Dihydralazine | 0.337 | 1.0 |

[1] Rats under urethane narcosis; intraperitoneal administration. ED 20% (mg/kg) = the dose which lowers the blood pressure by 20%.
[2] R.A. = relative activity; dihydralazine = 1.00

TABLE 3

Inhibition of thrombocyte aggregation, and anti-hypertensive effect, after oral administration

| Compound Example No. | Inhibition of thrombocyte aggregation[1] | | Anti-hypertensive effect[2] | |
|---|---|---|---|---|
| | ED 33% | R.A. | ED 20% | R.A. |
| 7 | 30.7 | 4.36 | 8.65 | 0.79 |
| 13 | 2.50 | 53.60 | 2.78 | 2.46 |
| 11 | 1.48 | 90.54 | 10.0 | 0.69 |
| 20 | 3.74 | 35.83 | 10.0 | 0.69 |
| Acetylsalicylic acid | 134 | 1.00 | — | — |
| Dihydralazine | — | — | 6.85 | 1.00 |

[1] Rats, oral administration ED 33% (mg/kg) = the dose which inhibits the collagen-induced aggregation by 33%. R.A. = relative activity, acetylsalicylic acid = 1.00
[2] Spontaneously hypertonic rats, oral administration. ED 20% (mg/kg) = the dose which lowers the blood pressure by 20% compared to the control group. R.A. of dihydralazine = 1.00

In respect of their pharmacological activity, the following compounds of the formula I may be singled out as examples: 2-(p-tolyl)-3,4-diaza-bicyclo[4.1.0]hept-2-en-5-one, 2-(p-methoxyphenyl)-3,4-diaza-bicyclo[4.1.0]hept-2-en-5-one, 2-(p-chlorophenyl)-3,4-diaza-bicyclo[4.1.0]hept-2-en-5-one, 2-(p-aminophenyl)-3,4-diaza-bicyclo[4.1.0]hept-2-en-5-one, 2-(p-formylaminophenyl)-3,4-diaza-bicyclo[4.1.0]hept-2-en-5-one, 2-(p-butyrylaminophenyl)-3,4-diaza-bicyclo[4.1.0]hept-2-en-5-one, 2-[p-(2-methylbutyrylamino)-phenyl]-3,4-diaza-bicyclo[4.1.0]hept-2-en-5-one, 2-[p-(3-chloropropionylamino)-phenyl]-3,4-diaza-bicyclo[4.1.0]hept-2-en-5-one, 2-[p-(4-chlorobutyrylamino)-phenyl]-3,4-diaza-bicyclo[4.1.0]hept-2-en-5-one, 2-(p-dichloroacetylaminophenyl)-3,4-diaza-bicyclo[4.1.0]hept-2-en-5-one, 2-[p-(2-methylcyclopropylcarbonylamino)-phenyl]-3,4-diaza-bicyclo[4.1.0]hept-2-en-5-one, 2-[p-(2,2-dichloro-1-methylcyclopropylcarbonylamino)-phenyl]-3,4-diaza-bicyclo[4.1.0]hept-2-en-5-one, 2-(p-crotonoylaminophenyl)-3,4-diaza-bicyclo[4.1.0]hept-2-en-5-one, 2-(p-cyanophenyl)-3,4-diaza-bicyclo[4.1.0]hept-2-en-5-one, 2-(p-isobutyrylaminophenyl)-3,4-diaza-bicyclo[4.1.0]hept-2-en-5-one, 2-(p-bromopivaloylaminophenyl)-3,4-diaza-bicyclo[4.1.0]hept-2-en-5-one, 2-[p-(2,2-dichloropropionylamino)-phenyl]-3,4-diaza-bicyclo[4.1.0]hept-2-en-5-one, 2-(p-cyclohexylcarbonylaminophenyl)-3,4-diaza-bicyclo[4.1.0]-hept-2-en-5-one and 2-(p-benzoylaminophenyl)-3,4-diaza-bicyclo[4.1.0]hept-2-en-5-one.

Compounds of the formula I, where the radical S is an acylamino radical —NHCOR[1] in the p-position, and R[1] is alkyl of 1 to 4 carbon atoms, which is unsubstituted or has from one to three halogen substituents, or is cycloalkyl of 3 to 5 carbon atoms in the ring, which is unsubstituted or has from one to three halogen and/or methyl substituents, or is alkenyl of 2 to 4 carbon atoms, and therapeutic agents containing the said compounds, are preferred.

Amongst the last category of compounds, the following may be singled out specifically: 2-(p-acetylaminophenyl)-3,4-diaza-bicyclo[4.1.0]hept-2-en-5-one, 2-(p-propionylaminophenyl)-3,4-diaza-bicyclo[4.1.0]hept-2-en-5-one, 2-(p-chloroacetylaminophenyl)-3,4-diaza-bicyclo[4.1.0]hept-2-en-5-one, 2-[p-(2-chloropropionylamino)-phenyl]-3,4-diaza-bicyclo[4.1.0]hept-2-en-5-one, 2-(p-cyclopropylcarbonylaminophenyl)-3,4-diaza-bicyclo[4.1.0]hept-2-en-5-one, 2-(p-acryloylaminophenyl)-3,4-diaza-bicyclo[4.1.0]hept-2-en-5-one and 2-(p-cyclobutylcarbonylaminophenyl)-3,4-diaza-bicyclo[4.1.0]hept-2-en-5-one.

The therapeutic agents or formulations are prepared in a conventional manner by compounding an appropriate dose with the conventional pharmaceutical carriers or diluents and the conventional pharmaceutical auxiliaries, in accordance with the desired route of administration. Suitable doses for man are from 1 to 100 mg, preferably from 5 to 50 mg, oral administration being preferred.

Examples of formulations suitable for oral administration are tablets, film tablets, dragees, capsules, pills, powders, solutions, suspensions or forms which exert a depot effect.

For practical use, the compounds to be used according to the invention are compounded with the solid or liquid carriers conventionally used in pharmaceutical production. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, eg. corn starch, alginic acid or polyvinylpyrrolidone, binders, eg. starch or gelatin, lubricants, eg. magnesium stearate or talc, and/or agents added to achieve a depot effect, eg. carboxypolymethylene, carboxymethylcellulose, celluloseacetate phthalate or polyvinyl acetate. The tablets can also consist of several layers.

Accordingly, dragees may be prepared by coating cores, prepared similarly to the tablets, with materials conventionally used in dragee coatings, for example collidone or shellac, gum arabic, talc, titanium dioxide or sugar. The dragee shell can also consist of several layers, in which case the auxiliaries mentioned above in connection with tablets may be used.

The Examples which follow illustrate the preparation of the novel 2-aryl-3,4-diaza-bicyclo[4.1.0]hept-2-en-5-ones.

EXAMPLE 1

(a) 18 ml (0.23 mole) of dimethylformamide are added dropwise in the course of a few minutes, whilst stirring, to 120 g (0.90 mole) of anhydrous aluminum chloride, resulting in a strongly exothermic reaction. 8.2 g (89.0 millimoles) of toluene are then added dropwise at 60°–70° C. Thereafter, 10.0 g (89.2 millimoles) of 1,2-cyclopropanedicarboxylic acid anhydride are added, a little at a time, at the same temperature, and the mixture is stirred for a further hour at 70° C. The melt is then introduced into 1 kg of ice. The solid which has precipitated is filtered off, washed with water and dried under reduced pressure at 50° C. 16.3 g (90% of theory) of cis-2-(p-toluoyl)-cyclopropanecarboxylic acid are obtained as colorless crystals, of melting point 165°–166° C. after recrystallization from ethyl acetate.

Analysis for $C_{12}H_{12}O_3$: calculated: C 70.6, H 5.9%: found: C 70.6, H 6.0%.

(b) 5.5 g (26.9 millimoles) of cis-2-(p-toluoyl)-cyclopropanecarboxylic acid, 1.5 g (30.0 millimoles) of hydrazine hydrate and 100 ml of ethanol are refluxed for 6 hours. The mixture is then concentrated and the residue is recrystallized from ethyl acetate. 4.3 g (80% of theory) of 2-(p-tolyl)-3,4-diaza-bicyclo[4.1.0]-hept-2-en-5-one are obtained as colorless crystals of melting point 162°–163.5° C.

Analysis for $C_{12}H_{12}N_2O$: calculated: C 72.0, H 6.0, N 14.0, O 8.0%: found: C 71.9, H 5.8, N 14.2, O 8.4%.

EXAMPLE 2

(a) 14.3 g (89.2 millimoles) of cyclohexylbenzene are added dropwise to 23.7 g (0.18 mole) of anhydrous aluminum chloride in 50 ml of nitrobenzene at 10°–15° C., whilst stirring. 10.0 g (89.2 millimoles) of 1,2-cyclopropanedicarboxylic acid anhydride are then added, a little at a time, at the same temperature and thereafter the mixture is stirred for 20 hours at room temperature, followed by 1 hour at 50° C. The solution is introduced into a mixture of 500 g of ice and 50 ml of concentrated hydrochloric acid. The nitrobenzene is removed by steam distillation and the solid which has precipitated is filtered off at 10° C. and dissolved in aqueous sodium carbonate solution. The solution is filtered and the filtrate is acidified with concentrated hydrochloric acid. The solid which precipitates is filtered off, washed with water and dried under reduced pressure at 50° C. 19.9 g (82% of theory) of cis-2-(p-cyclohexylbenzoyl)-cyclopropanecarboxylic acid are obtained as almost colorless crystals of melting point 162°–163° C. after recrystallization from methanol.

Analysis for $C_{17}H_{20}O_3$: calculated: C 75.0, H 7.4, O 17.6%: found: C 74.9, H 7.5, O 17.4%.

(b) 8.0 g (29.4 millimoles) of cis-2-(p-cyclohexylbenzoyl)-cyclopropanecarboxylic acid, 1.6 g (32.0 millimoles) of hydrazine hydrate and 100 ml of ethanol are refluxed for 8 hours. The product is filtered off at 0° C. and dried under reduced pressure at 50° C. 7.3 g (93% of theory) of 2-(p-cyclohexylphenyl)-3,4-diaza-bicyclo[4.1.0]hept-2-en-5-one are obtained as almost colorless crystals, of melting point 211°–212° C. after recrystallization from isopropanol.

Analysis for $C_{17}H_{20}N_2O$: calculated: C 76.1, H 7.5, N 10.4, O 6.0%: found: C 76.1, H 7.2, N 10.8, O 6.3%.

EXAMPLE 3

(a) Example 2a is repeated with 9.6 g (88.8 millimoles) of anisole in place of cyclohexylbenzene. After working up, 14.2 g (73% of theory) of cis-2-(p-methoxybenzoyl)-cyclopropanecarboxylic acid are obtained as colorless crystals, melting point 170°–172° C. after recrystallization from methanol.

Analysis for $C_{12}H_{12}O_4$: calculated: C 65.4, H 5.5, O 29.1%: found: C 65.3, H 5.5, O 28.5%.

(b) 6.0 g (27.2 millimoles) of cis-2-(p-methoxybenzoyl)-cyclopropanecarboxylic acid, 1.36 g (27.2 millimoles) of hydrazine hydrate and 100 ml of ethanol are refluxed for 6 hours. After filtering off the product at 0° C. and recrystallizing it from methanol, 5.2 g (88% of theory) of 2-(p-methoxyphenyl)-3,4-diazabicyclo[4.1.0]-]hept-2-en-5-one are obtained as colorless crystals, of melting point 174°–175° C.

Analysis for $C_{12}H_{12}N_2O_2$: calculated: C 66.7, H 5.6, N 13.0, O 14.8%: found: C 66.8, H 5.7, N 13.1, O 15.2%.

EXAMPLE 4

(a) 12.7 g (82.4 millimoles) of biphenyl, followed by 10.0 g (89.2 millimoles) of 1,2-cyclopropanedicarboxylic acid anhydride, are added, in each case a little at a time, to 29.7 g (0.22 mole) of anhydrous aluminum chloride in 100 ml of carbon disulfide whilst stirring at room temperature. The mixture is refluxed for 4 hours and then left to stand for 2 days at ambient temperature. After decanting the carbon disulfide, the reaction mixture is introduced into 200 g of ice and 50 ml of concentrated hydrochloric acid. The solid which precipitates is filtered off, washed with water and recrystallized from propanol. 6.9 g (31% of theory) of cis-2-(p-biphenylcarbonyl)-cyclopropanecarboxylic acid are obtained as colorless crystals, of melting point 222°–223° C. after a further recrystallization, from ethanol.

Analysis for $C_{17}H_{14}O_3$: calculated: C 76.7, H 5.3, O 18.0%: found: C 76.5, H 4.9, O 18.1%.

(b) 7.0 g (26.3 millimoles) of cis-2-(p-biphenylcarbonyl)-cyclopropanecarboxylic acid, 1.45 g (29.0 millimoles) of hydrazine and 100 ml of ethanol are refluxed for 8 hours. After filtering off the product at 0° C. and drying it under reduced pressure at 50° C., 6.6 g (96% of theory) of 2-(p-biphenylyl)-3,4-diazabicyclo[4.1.0]hept-2-en-5-one are obtained as colorless crystals, of melting point 220°–221° C. after recrystallization from ethanol.

Analysis for $C_{17}H_{14}N_2O$: calculated: C 77.8, H 5.4, N 10.7, O 6.1%: found: C 77.2, H 5.3, N 10.8, O 6.6%.

EXAMPLE 5

(a) Using the method described in Example 1a, 9.0 g (80.0 millimoles) of chlorobenzene are reacted with 10.0 g (89.2 millimoles) of 1,2-cyclopropanedicarboxylic acid anhydride in the presence of 120 g of aluminum chloride and 18 ml of dimethylformamide. The melt is introduced into 1 kg of ice and 120 ml of concentrated hydrochloric acid. The solid which has precipitated is filtered off, washed with water and dried under reduced pressure at 50° C. After recrystallization from ethyl acetate, 12.6 g (70% of theory) of cis-2-(p-chlorobenzoyl)-cyclopropanecarboxylic acid are obtained as colorless crystals, of melting point 162°–164° C.

Analysis for $C_{11}H_9ClO_3$: calculated: C 58.8, H 4.0, Cl 15.8, O 21.4%: found: C 58.5, H 3.8, Cl 15.9, O 21.4%.

(b) 6.0 g (26.7 millimoles) of cis-2-(p-chlorobenzoyl)-cyclopropanecarboxylic acid, 1.47 g (29.4 millimoles) of hydrazine hydrate and 150 ml of ethanol are refluxed for 6 hours. The mixture is concentrated to about 20 ml and the product is filtered off at 0° C. and recrystallized from methanol. 4.7 g (80% of theory) of 2-(p-chlorophenyl)-3,4-diaza-bicyclo[4.1.0]hept-2-en-5-one are obtained as colorless crystals, of melting point 199°–200° C.

Analysis for $C_{11}H_9ClN_2O$: calculated: C 59.9, H 4.1, Cl 16.1, N 12.7, O 7.3%: found: C 59.8, H 4.1, Cl 16.2, N 12.9, O 7.5%.

EXAMPLE 6

(a) Example 5a is repeated with 8.6 g (89.5 millimoles) of fluorobenzene in place of chlorobenzene. After recrystallization from an ethyl acetate/petroleum ether mixture, 10.2 g (55% of theory) of cis-2-(p-fluorobenzoyl)-cyclopropanecarboxylic acid are obtained as almost colorless crystals of melting point 128°–129° C.

Analysis for $C_{11}H_9FO_3$: calculated: C 63.5, H 4.4, F 9.1% found: C 63.5, H 4.5, F 9.0%.

(b) 6.0 g (28.8 millimoles) of cis-2-(p-fluorobenzoyl)-cyclopropanecarboxylic acid, 1.44 g (28.8 millimoles) of hydrazine hydrate and 100 ml of ethanol are refluxed for 6 hours. After filtering off the product at 0° C. and recrystallizing it from methanol, 4.3 g (73% of theory) of 2-(p-fluorophenyl)-3,4-diaza-bicyclo[4.1.0]hept-2-en-5-one are obtained as almost colorless crystals, of melting point 192°–193° C.

Analysis for $C_{11}H_9FN_2O$: calculated: C 64.7, H 4.4, F 9.3, N 13.7%: found: C 64.5, H 4.6, F 9.1, N 13.9%.

EXAMPLE 7

(a) Example 4a is repeated with 11.1 g (82.1 millimoles) of acetanilide instead of biphenyl. After recrystallization from methanol, 5.1 g (25% of theory) of cis-2-(p-acetylaminobenzoyl)-cyclopropanecarboxylic acid are obtained as almost colorless crystals, of melting point 227°–228° C.

Analysis for $C_{13}H_{13}NO_4$: calculated: C 63.2, H 5.3, N 5.7, O 25.9%: found: C 63.0, H 5.5, N 5.9, O 24.9%.

(b) 18 ml (0.23 mole) of dimethylformamide are added dropwise in the course of a few minutes, whilst stirring, to 120 g (0.90 mole) of anhydrous aluminum chloride, resulting in a strongly exothermic reaction. A mixture of 12.0 g (88.8 millimoles) of acetanilide and 10.0 g (89.2 millimoles) of 1,2-cyclopropanedicarboxylic acid anhydride is then added, a little at a time, at 60°–70° C., after which the mixture is stirred for a further hour at 70° C. On working up as described in Example 1a, and recrystallizing the product from methanol, 13.7 g (62% of theory) of cis-2-(p-acetylaminobenzoyl)-cyclopropanecarboxylic acid are obtained as beige crystals, which are identical with the compound from Example 7a.

(c) 6.0 g (24.3 millimoles) of cis-2-(p-acetylaminobenzoyl)-cyclopropanecarboxylic acid, 1.33 g (26.6 millimoles) of hydrazine hydrate and 150 ml of ethanol are refluxed for 6 hours. After filtering off the product at 0° C. and drying it under reduced pressure at 50° C., 5.0 g (85% of theory) of 2-(p-acetylaminophenyl)-3,4-diaza-bicyclo[4.1.0]hept-2-en-5-one are isolated as colorless crystals, melting point 269°–270° C. after recrystallization from a methanol/water mixture.

Analysis for $C_{13}H_{13}N_3O_2$: calculated: C 64.2, H 5.4, N 17.3, O 13.2%: found: C 64.0, H 5.5, N 17.3, O 13.5%.

EXAMPLE 8

(a) 25 g (103 millimoles) of 2-(p-acetylaminophenyl)-3,4-diaza-bicyclo[4.1.0]hept-2-en-5-one (see Example 7c), 215 ml of methanol and 215 ml of 10 N sodium hydroxide solution are refluxed for 3 hours. The methanol is then stripped off under reduced pressure. 500 ml of water are added to the residue and the mixture is brought to pH 4 with dilute hydrochloric acid. After filtering off the product and drying under reduced pressure at 50° C., 19.3 g (93% of theory) of 2-(p-aminophenyl)-3,4-diaza-bicyclo[4.1.0]hept-2-en-5-one are isolated as almost colorless crystals, of melting point 230°–231° C. after recrystallization from methanol.

Analysis for $C_{11}H_{11}N_3O$: calculated: C 65.7, H 5.5, N 20.9%: found: C 65.3, H 5.5, N 21.1%.

(b) 6.0 g (29.8 millimoles) of the amino compound obtained above are dissolved in 50 ml of 10 percent strength aqueous hydrochloric acid at 50° C. The mixture is cooled to 0° C. and the solid which precipitates is filtered off. After recrystallization from methanol/ether, 5.2 g (73% of theory) of 2-(p-aminophenyl)-3,4-diaza-bicyclo[4.1.0]hept-2-en-5-one hydrochloride are isolated as almost colorless crystals, of melting point 288°–290° C.

Analysis for $C_{11}H_{12}ClN_3O$: calculated: C 55.6, H 5.1, Cl 14.9, N 17.7, O 6.7%: found: C 55.6, H 5.2, Cl 14.8, N 17.6, O 6.9%.

EXAMPLE 9

(a) 95 g (384 millimoles) of cis-2-(p-acetylaminobenzoyl)-cyclopropanecarboxylic acid (see Example 7b) and 600 ml of 6 N hydrochloric acid are kept at 90°–95° C. for about 30 minutes. The solution is then brought to pH 4, at 10° C., by adding dilute sodium hydroxide solution. The solid which precipitates is filtered off and washed with water. After recrystallization from water, 46.4 g (59% of theory) of cis-2-(p-aminobenzoyl)-cyclopropanecarboxylic acid are isolated as pale grey crystals of melting point 190°–191° C.

Analysis for $C_{11}H_{11}NO_3$: calculated: C 64.4, H 5.4, N 6.8%: found: C 64.4, H 5.3, N 7.0%.

(b) 20 g (97.5 millimoles) of cis-2-(p-aminobenzoyl)-cyclopropanecarboxylic acid, 5.9 g (118 millimoles) of hydrazine hydrate and 100 ml of ethanol are refluxed for 5 hours. After filtering off the product at 10° C. and drying it under reduced pressure at 50° C., 18.6 g (95% of theory) of 2-(p-aminophenyl)-3,4-diaza-bicyclo[4.1.0]-hept-2-en-5-one are obtained as pale yellow crystals, which are identical with the compound from Example 8a.

EXAMPLE 10

6.0 g (29.8 millimoles) of 2-(p-aminophenyl)-3,4-diaza-bicyclo[4.1.0]hept-2-en-5-one (see Example 8a) and 30 ml of formic acid are refluxed for 1 hour. The solution is then poured into 500 ml of water and the precipitate which separates out is filtered off, washed with water and recrystallized from a methanol/water mixture. 4.6 g (67% of theory) of 2-(p-formylaminophenyl)-3,4-diaza-bicyclo[4.1.0]hept-2-en-5-one are isolated as almost colorless crystals, of melting point 239°–240° C.

Analysis for $C_{12}H_{11}N_3O_2$: calculated: C 62.9, H 4.8, N 18.3, O 14.0%: found: C 62.7, H 4.9, N 18.6, O 14.3%.

EXAMPLE 11

6.0 g (29.8 millimoles) of 2-(p-aminophenyl)-3,4-diaza-bicyclo[4.1.0]hept-2-en-5-one (see Example 9b), 4.2 g (45.4 millimoles) of propionyl chloride and 100 ml of anhydrous toluene are kept at 80° C. for 6 hours. The product is then filtered off at 10° C., washed first with toluene and then with water, and dried under reduced pressure at 50° C. 6.5 g (83% of theory) of 2-(p-propionylaminophenyl)-3,4-diaza-bicyclo[4.1.0]hept-2-en-5-one, hydrated with one mole of water per four moles of compound, are obtained as almost colorless crystals, of melting point 252°–253° C. after recrystallization from a dimethylformamide/water mixture.

Analysis for $C_{14}H_{15}N_3O_2 \cdot \frac{1}{4}H_2O$: calculated: C 64.2, H 6.0, N 16.1%: found: C 64.2, H 5.8, N 16.4%.

EXAMPLE 12

Example 11 is repeated with 3.7 g (32.8 millimoles) of chloroacetyl chloride instead of propionyl chloride. After recrystallizing the product from water, 7.5 g (91% of theory) of 2-(p-chloroacetylaminophenyl)-3,4-diaza-bicyclo[4.1.0]hept-2-en-5-one are obtained as pale yellow crystals, of melting point 220°–221° C.

Analysis for $C_{13}H_{12}ClN_3O_2$: calculated: C 56.2, H 4.4, Cl 12.8, N 15.1, O 11.5%: found: C 55.8, H 4.2, Cl 12.7, N 15.2, O 12.2%.

EXAMPLE 13

Example 11 is repeated using 4.65 g (44.5 millimoles) of cyclopropanecarboxylic acid chloride instead of propionyl chloride. After recrystallizing the product from a dimethylformamide/water mixture, 4.5 g (54% of theory) of 2-(p-cyclopropylcarbonylaminophenyl)-3,4-diaza-bicyclo[4.1.0]hept-2-en-5-one hemihydrate are isolated as beige crystals, of melting point 277°–279° C.

Analysis for $C_{15}H_{15}N_3O_2 \cdot \frac{1}{2}H_2O$: calculated: C 64.7, H 5.8, N 15.1%: found: C 65.0, H 5.4, N 15.3%.

EXAMPLE 14

Using a method similar to Example 11, 6.0 g (29.8 millimoles) of 2-(p-aminophenyl)-3,4-diaza-bicyclo[4.1.0]hept-2-en-5-one (see Example 8a) are reacted with 4.05 g (44.7 millimoles) of acryloyl chloride in toluene. The product is filtered off at 10° C., washed first with toluene and then with water, and recrystallized from a dimethylformamide/water mixture. 3.5 g (45% of theory) of 2-(p-acryloylaminophenyl)-3,4-diaza-bicyclo[4.1.0]hept-2-en-5-one, hydrated with one mole of water per four moles of compound, are isolated as almost colorless crystals of melting point 240°–241° C.

Analysis for $C_{14}H_{13}N_3O_2 \cdot \frac{1}{4}H_2O$: calculated: C 64.7, H 5.2, N 16.2, O 13.9%: found: C 64.5, H 4.9, N 16.2, O 13.0%.

The Table which follows lists Examples 15 to 30. These diaza-bicyclo[4.1.0]heptenones are prepared by the method described in Example 11.

TABLE $R^1CONH$—[structure with phenyl, N—N H, bicyclic ring, =O]

| Example | $R^1$ | Melting point [°C.] | Analysis (%) C | H | Cl | N | O |
|---|---|---|---|---|---|---|---|
| 15 | $CH_3$—$CH_2$—$CH_2$— | 241–242 (DMF/water) | calc.: 66.4 found: 65.9 | 6.3 6.4 | — — | 15.5 16.0 | |
| 16 | $(CH_3)_2CH$— | 277–278 (. ½ $H_2O$) (DMF/water) | calc.: 64.3 found: 64.6 | 6.5 6.3 | — — | 15.0 15.2 | |
| 17 | $CH_3$—$CH_2$—$CH_2$—$CH_2$— | 207–208 (DMF/water) | calc.: 67.3 found: 66.9 | 6.7 6.8 | — — | 14.7 14.7 | |
| 18 | $CH_3$—$CH_2$—$CH(CH_3)$— | 227–228 (DMF/water) | calc.: 67.3 found: 67.1 | 6.7 6.7 | — — | 14.7 15.0 | |
| 19 | Cl—$CH_2$—$CH_2$— | from 215, with decomposition (DMF/water) | calc.: 57.6 found: 57.3 | 4.8 5.0 | 12.2 11.5 | 14.4 14.5 | |
| 20 | $CH_3$—$CHCl$— | 236–237 (ethanol) | calc.: 57.6 found: 57.6 | 4.8 5.2 | 12.2 12.2 | 14.4 14.3 | 11.0 11.4 |
| 21 | Cl—$CH_2$—$CH_2$—$CH_2$— | 206–207 (DMF/water) | calc.: 58.9 found: 59.1 | 5.3 5.3 | 11.6 11.2 | 13.7 14.0 | — |
| 22 | Br—$CH_2$—$C(CH_3)_2$— | 211–212 ($CH_3OH$/acetone) | calc.: 52.8 found: 53.1 | 5.0 5.0 | 21.9 20.9 | 11.5 12.0 | — |
| 23 | $Cl_2CH$— | from 251, with decomposition (propanol) | calc.: 50.0 found: 50.1 | 3.6 3.9 | 22.7 22.4 | 13.5 13.7 | — |
| 24 | $CH_3$—$CCl_2$— | 235–237 (decompostion) (propanol) | calc.: 51.6 found: 51.8 | 4.0 4.1 | 21.7 21.2 | 12.9 13.3 | — |
| 25 | cyclopropyl-$CH_3$ | 268–269 (ethanol) | calc.: 67.8 found: 67.4 | 6.0 6.0 | — — | 14.8 14.8 | — |
| 26 | $Cl_2C(CH_3)$—cyclopropyl | 238–239 (decomposition) (DMF/water) | calc.: 54.6 found: 54.7 | 4.3 4.3 | 20.1 19.6 | 11.9 12.2 | — |

TABLE-continued

R¹CONH—⟨phenyl⟩—⟨bicyclic structure with N—N, H, =O⟩

| Example | R¹ | Melting point [°C.] | Analysis (%) calc./found | C | H | Cl | N | O |
|---|---|---|---|---|---|---|---|---|
| 27 | cyclobutyl | 276–277 (ethanol/water) | calc.: found: | 67.8 67.4 | 6.0 5.9 | — — | 14.8 14.6 | — — |
| 28 | cyclohexyl | 272–273 (DMF/water) | calc.: found: | 69.4 69.0 | 6.8 6.8 | — — | 13.5 13.5 | — — |
| 29 | CH₃—CH=CH— cis:trans ≃ 10:90 | 232–233 (.¼ H₂O) (methanol/water) | calc.: found: | 65.8 65.7 | 5.7 5.8 | — — | 15.3 15.5 | 13.1 12.7 |
| 30 | cyclohexadienyl | 268–270 (.½ H₂O) (DMF/water) | calc.: found: | 68.8 69.0 | 5.1 4.8 | — — | 13.4 13.7 | — — |

EXAMPLE 31

(a) 5.0 g (24.4 millimoles) of cis-2-(p-aminobenzoyl)-cyclopropanecarboxylic acid (see Example 9a) and 50 ml of propionic anhydride are kept at 80° C. for 30 minutes. The solution is then poured into ice water. The oil which hereupon separates out is left to stand overnight at room temperature in the aqueous phase, during which time it solidifies. It is then filtered off, washed with water and recrystallized from ethyl acetate/petroleum ether. 1.9 g (30% of theory) of cis-2-(p-propionylaminobenzoyl)-cyclopropanecarboxylic acid are isolated as colorless crystals of melting point 182°–183° C.

Analysis for C₁₄H₁₅NO₄: calculated: C 64.4, H 5.8, N 5.4%; found: C 64.3, H 6.0, N 5.3%.

(b) 1.0 g (3.8 millimoles) of cis-2-(p-propionylaminobenzoyl)-cyclopropanecarboxylic acid, 0.22 g (4.4 millimoles) of hydrazine hydrate and 20 ml of ethanol are refluxed for 5 hours. After filtering off the product at 25° C. and drying it under reduced pressure at 50° C., 0.8 g (81% of theory) of 2-(p-propionylaminophenyl)-3,4-diaza-bicyclo[4.1.0]hept-2-en-5-one are obtained as almost colorless crystals, of melting point 268°–270° C.

Analysis for C₁₄H₁₅N₃O₂: calculated: C 65.4, H 5.9, N 16.3%; found: C 65.3, H 5.9, N 16.5%.

EXAMPLE 32

(a) A solution of 90 g (0.47 mole) of cis-2-benzoylcyclopropanecarboxylic acid in 750 ml of concentrated nitric acid is added dropwise to 750 ml of concentrated sulfuric acid whilst stirring at 25°–30° C., and the mixture is then stirred for 2 hours at room temperature. The solution is poured onto 4 kg of ice and the mixture is extracted with methylene chloride. The extract is washed with water, dried and concentrated. After recrystallizing the residue from water, 86 g (72% of theory) of cis-2-(m-nitrobenzoyl)-cyclopropanecarboxylic acid hydrate are obtained as colorless crystals, of melting point 96°–98° C.

Analysis for C₁₁H₁₁NO₆: calculated: C 52.2, H 4.4, N 5.5%; found: C 52.4; H 4.6, N 5.6%.

(b) 4.4 g (17.4 millimoles) of cis-2-(m-nitrobenzoyl)-cyclopropanecarboxylic acid hydrate, 1.05 g (21.0 millimoles) of hydrazine hydrate and 100 ml of ethanol are refluxed for 7 hours. After filtering off the product at 10° C. and drying it under reduced pressure at 50° C., 2.8 g (70% of theory) of 2-(m-nitrophenyl)-3,4-diazabicyclo[4.1.0]hept-2-en-5-one are obtained as pale yellow crystals, of melting point 220°–221° C.

Analysis for C₁₁H₉N₃O₃: calculated: C 57.1, H 3.9, N 18.2, O 20.8%; found: C 57.3, H 4.2, N 18.5, O 20.7%.

EXAMPLE 33

20.4 g (88.2 millimoles) of 2-(m-nitrophenyl)-3,4-diaza-bicyclo[4.1.0]hept-2-en-5-one (see Example 32b), 300 ml of ethanol, 150 ml of cyclohexene and 4.2 g of 10% strength palladium on charcoal are refluxed for 12 hours. The catalyst is filtered off, the filtrate is concentrated and the residue is recrystallized from ethyl acetate/methanol. 8.5 g (48% of theory) of 2-(m-aminophenyl)-3,4-diaza-bicyclo[4.1.0]hept-2-en-5-one are obtained as beige crystals, of melting point 192°–193° C.

Analysis for C₁₁H₁₁N₃O: calculated: C 65.7, H 5.5, N 20.9%; found: C 65.6, H 5.5, N 21.2%.

EXAMPLE 34

1.5 g (6.5 millimoles) of 2-(m-nitrophenyl)-3,4-diazabicyclo[4.1.0]hept-2-en-5-one (see Example 32b), dissolved in 80 ml of tetrahydrofuran, are hydrogenated with 0.5 g of 10% strength palladium on charcoal at room temperature. When the hydrogen absorption has ceased, the catalyst is filtered off and the filtrate is concentrated. The residue is recrystallized from an ethyl acetate/methanol mixture. 0.9 g (69% of theory) of 2-(m-aminophenyl)-3,4-diaza-bicyclo[4.1.0]hept-2-en-5-one is obtained as colorless crystals, which are identical with the compound from Example 33.

EXAMPLE 35

A solution of 0.65 g (13.0 millimoles) of hydrazine hydrate in 10 ml of ethanol is added, whilst stirring, to a mixture of 1.5 g (6.5 millimoles) of 2-(m-nitrophenyl)-3,4-diaza-bicyclo[4.1.0]hept-2-en-5-one (see Example 32b), 20 ml of ethanol and a small amount of an aqueous Raney nickel suspension in the course of 5 minutes, during which the temperature rises from 25° to 35° C. Stirring is continued for 1 hour and the reaction mixture is then slowly raised to the boil. It is refluxed for 5 minutes and filtered hot, and the filtrate is concentrated. After recrystallization from ethyl acetate/methanol, 1.0 g (76% of theory) of 2-(m-aminophenyl)-3,4-diaza-bicyclo[4.1.0]hept-2-en-5-one is obtained as colorless crystals, identical with the compound from Example 33.

EXAMPLE 36

(a) A mixture of 0.14 ml of water, 6.4 g of iron powder and 0.64 ml of acetic acid is refluxed for 15 minutes. It is then diluted with 35 ml of water, after which 5 g (19.7 millimoles) of cis-2-(m-nitrobenzoyl)-cyclopropanecarboxylic acid hydrate (see Example 32a) are added, a little at a time, at the boiling point of the reaction mixture. The mixture is then refluxed for two hours. 5.3 ml of concentrated ammonia solution are added and the batch is filtered hot. The filtrate is brought to pH 4 with dilute hydrochloric acid and is concentrated under reduced pressure to a volume of about 20 ml. After filtering off the product, 2.3 g (57% of theory) of cis-2-(m-aminobenzoyl)-cyclopropanecarboxylic acid are obtained as colorless crystals, of melting point 133°-134° C. after recrystallization from water.

Analysis for $C_{11}H_{11}NO_3$: calculated: C 64.4, H 5.4, N 6.8%: found: C 64.2, H 5.5, N 6.6%.

(b) 600 mg (2.9 millimoles) of cis-2-(m-aminobenzoyl)-cyclopropanecarboxylic acid, 20 ml of ethanol and 0.16 g (3.2 millimoles) of hydrazine hydrate are refluxed for 6 hours. After filtering off the product at 10° C. and drying it under reduced pressure at 50° C., 0.35 g (60% of theory) of 2-(m-aminophenyl)-3,4-diaza-bicyclo[4.1.0]hept-2-en-5-one are isolated as colorless crystals, which are identical with the compound from Example 33.

EXAMPLE 37

6.0 g (29.8 millimoles) of 2-(m-aminophenyl)-3,4-diaza-bicyclo[4.1.0]hept-2-en-5-one (see Example 33), 3.5 g (44.6 millimoles) of acetyl chloride and 100 ml of anhydrous toluene are kept at 80° C. for 6 hours. The product is filtered off at 10° C., washed first with toluene and then with water, and recrystallized from methanol. 2.9 g (40% of theory) of 2-(m-acetylaminophenyl)-3,4-diaza-bicyclo[4.1.0]hept-2-en-5-one are obtained as almost colorless crystals, of melting point 200°-202° C.

Analysis for $C_{13}H_{13}N_3O_2$: calculated: C 64.2, H 5.4, N 17.3%: found: C 64.1, H 5.4, N 17.6%.

EXAMPLE 38

Example 37 is repeated using 5.1 g of chloroacetyl chloride (45.2 millimoles) instead of acetyl chloride. After recrystallizing the product from methanol, 4.5 g (54% of theory) of 2-(m-chloroacetylaminophenyl)-3,4-diaza-bicyclo[4.1.0]hept-2-en-5-one are isolated as colorless crystals, of melting point 166°-169° C.

Analysis for $C_{13}H_{12}ClN_3O_2$: calculated: C 56.2, H 4.4, Cl 12.8, N 15.1%: found: C 56.1, H 4.5, Cl 12.9, N 15.1%.

EXAMPLE 39

A cold solution of 2.4 g (34.8 millimoles) of sodium nitrite in 20 ml of water is added to a solution of 7.0 g (34.8 millimoles) of 2-(p-aminophenyl)-3,4-diaza-bicyclo[4.1.0]hept-2-en-5-one (see Example 8a) in 26 ml of concentrated hydrochloric acid and 260 ml of water whilst stirring at 0° C. The mixture is then stirred for a further 10 minutes, at 0°-5° C., after which it is neutralized with sodium carbonate at the same temperature. The resulting solution is added dropwise, whilst stirring, to a cold (0°-5° C.) solution of 3.9 g (43.5 millimoles) of copper-(I) cyanide and 7.0 g (107.5 millimoles) of potassium cyanide in 175 ml of water, covered with a layer of 85 ml of toluene. The mixture is then stirred for 30 minutes at 5° C., followed by 20 hours at room temperature. After filtering off the product and drying it under reduced pressure at 50° C., 6.6 g (90% of theory) of 2-(p-cyanophenyl)-3,4-diaza-bicyclo[4.1.0-]hept-2-en-5-one are obtained as brown crystals, of melting point 265°-266° C. after recrystallization from acetonitrile.

Analysis for $C_{12}H_9N_3O$: calculated: C 68.2, H 4.3, N 19.9, O 7.6%: found: C 67.6, H 4.5, N 20.4, O 7.5%.

EXAMPLE 40

(a) A cold solution of 3.4 g (49.3 millimoles) of sodium nitrite in 25 ml of water is added to a solution of 10.0 g (48.7 millimoles) of cis-2-(p-aminobenzoyl)-cyclopropanecarboxylic acid (see Example 9a) in 37 ml of concentrated hydrochloric acid and 190 ml of water, whilst stirring at 0° C. The mixture is then stirred for a further 10 minutes, at 0°-5° C., after which it is neutralized with sodium carbonate at the same temperature. The solution obtained is added dropwise, whilst stirring, to a cold (0°-5° C.) solution of 5.3 g (59.2 millimoles) of copper-(I) cyanide and 7.5 g (115.2 millimoles) of potassium cyanide in 150 ml of water, which is covered with a layer of 40 ml of toluene. The mixture is then stirred for 30 minutes at 5° C., followed by 12 hours at room temperature. It is filtered and the filtrate is acidified with concentrated hydrochloric acid. The solid which precipitates is filtered off, washed with water and extracted with hot ethanol. Concentrating the ethanol extract gives 3.5 g (33% of theory) of cis-2-(p-cyanobenzoyl)-cyclopropanecarboxylic acid as pale brown crystals, of melting point 180°-182° C.

(b) 2.45 g (11.4 millimoles) of cis-2-(p-cyanobenzoyl)-cyclopropanecarboxylic acid, 0.57 g (11.4 millimoles) of hydrazine hydrate and 50 ml of ethanol are refluxed for 6 hours. After filtering off the product at 10° C. and drying it under reduced pressure at 50° C., 1.6 g (67% of theory) of 2-(p-cyanophenyl)-3,4-diaza-bicyclo[4.1.0-]hept-2-en-5-one are obtained as ocher crystals which are identical with the compound from Example 39.

EXAMPLE 41

Example 39 is repeated, using 7.0 g (34.8 millimoles) of 2-(m-aminophenyl)-3,4-diaza-bicyclo[4.1.0]hept-2-en-5-one (see Example 33) instead of 2-(p-aminophenyl)-3,4-diaza-bicyclo[4.1.0]hept-2-en-5-one. After recrystallizing the product from a methanol/water mixture, 5.7 g (78% of theory) of 2-(m-cyanophenyl)-3,4-diaza-bicyclo[4.1.0]hept-2-en-5-one are obtained as pale brown crystals, of melting point 205°-206° C.

Analysis for $C_{12}H_9N_3O$: calculated: C 68.2, H 4.3, N 19.9%: found: C 67.9, H 4.3, N 20.3%.

EXAMPLE 42

10.0 g (49.7 millimoles) of 2-(p-aminophenyl)-3,4-diaza-bicyclo[4.1.0]hept-2-en-5-one (see Example 8a), 6.6 g (49.9 millimoles) of 2,5-dimethoxytetrahydrofuran and 100 ml of acetic acid are refluxed for 4 hours. The product is filtered off at 10° C. and recrystallized from a dimethylformamide/water mixture. 5.2 g (41% of theory) of 2-[p-(pyrrol-1-yl)-phenyl]-3,4-diaza-bicyclo[4.1.0]hept-2-en-5-one, hydrated with one mole of water per four moles of compound, are obtained as beige crystals, of melting point 230°-231° C.

Analysis for $C_{15}H_{13}N_3O \cdot \frac{1}{4} H_2O$: calculated: C 70.4, H 5.3, N 16.4%: found: C 70.5, H 5.4, N 16.4%.

EXAMPLE 43

3.0 g (14.9 millimoles) of 2-(p-aminophenyl)-3,4-diaza-bicyclo[4.1.0]hept-2-en-5-one, 2.0 g (17.5 millimoles) of difluoroacetyl chloride and 100 ml of absolute tetrahydrofuran are kept first for 3 hours at 0°–5° C. and then for 20 hours at room temperature. The product is filtered off at 10° C., washed with water and recrystallized from methanol. 2.7 g (63% of theory) of 2-(p-difluoroacetylaminophenyl)-3,4-diaza-bicyclo[4.1.0]hept-2-en-5-one hemihydrate are obtained as colorless crystals, of melting point 223°–224° C.

Analysis for $C_{13}H_{11}F_2N_3O_2 \cdot \frac{1}{2} H_2O$: calculated: C 54.2, H 4.2, F 13.2, N 14.6%: found: C 54.3, H 4.3, F 13.2, N 14.7%.

EXAMPLE 44

5.0 g (24.8 millimoles) of 2-(p-aminophenyl)-3,4-diaza-bicyclo[4.1.0]hept-2-en-5-one and 30 ml of trifluoroacetic anhydride are refluxed for 1 hour. The product is filtered off at 10° C., washed first with toluene and then with water, and recrystallized from a dimethylformamide/water mixture. 5.1 g (69% of theory) of 2-(p-trifluoroacetylaminophenyl)-3,4-diaza-bicyclo[4.1.0]hept-2-en-5-one are isolated as colorless crystals, of melting point 242°–243° C.

Analysis for $C_{13}H_{10}F_3N_3O_2$: calculated: C 52.5, H 3.4, F 19.2, N 14.1%: found: C 52.5, H 3.6, F 18.9, N 14.3%.

EXAMPLE 45

6.0 g (29.8 millimoles) of 2-(p-aminophenyl)-3,4-diaza-bicyclo[4.1.0]hept-2-en-5-one, 4.2 g (35.4 millimoles) of 1-methylcyclopropanecarboxylic acid chloride and 150 ml of absolute tetrahydrofuran are refluxed for 7 hours. The product is filtered off at 10° C., washed with water and recrystallized twice from a dimethylformamide/water mixture. 4.5 g (53% of theory) of 2-[p-(1-methylcyclopropylcarbonylamino)-phenyl]-3,4-diaza-bicyclo[4.1.0]hept-2-en-5-one are obtained as pale beige crystals, of melting point 253°–255° C.

Analysis for $C_{16}H_{17}N_3O_2$: calculated: C 67.8, H 6.0, N 14.8%: found: C 67.5, H 6.0, N 15.1%.

EXAMPLE 46

6.0 g (29.8 millimoles) of 2-(p-aminophenyl)-3,4-diaza-bicyclo[4.1.0]hept-2-en-5-one, 4.7 g (35.4 millimoles) of 2,2-dimethylcyclopropanecarboxylic acid chloride and 150 ml of absolute tetrahydrofuran are refluxed for 10 hours. The reaction solution is then concentrated. After recrystallizing the residue from a dimethylformamide/water mixture, 6.7 g (75% of theory) of 2-[p-(2,2-dimethylcyclopropylcarbonylamino)-phenyl]-3,4-diaza-bicyclo[4.1.0]hept-2-en-5-one are isolated as almost colorless crystals, of melting point 250°–252° C.

Analysis for $C_{17}H_{19}N_3O_2$: calculated: C 68.7, H 6.4, N 14.1%: found: C 68.3, H 6.4, N 13.9%.

EXAMPLE 47

5.0 g (24.8 millimoles) of 2-(p-aminophenyl)-3,4-diaza-bicyclo[4.1.0]hept-2-en-5-one, 4.5 g (32.4 millimoles) of 1-chlorocyclopropanecarboxylic acid chloride and 100 ml of absolute tetrahydrofuran are kept at room temperature for 6 hours. The product is filtered off at 10° C., washed first with tetrahydrofuran and then with water, and recrystallized from methanol. 4.7 g (62% of theory) of 2-[p-(1-chlorocyclopropylcarbonylamino)-phenyl]-3,4-diaza-bicyclo[4.1.0]hept-2-en-5-one are isolated as colorless crystals, of melting point 221°–222° C.

Analysis for $C_{15}H_{14}ClN_3O_2$: calculated: C 59.3, H 4.6, Cl 11.7, N 13.8%: found: C 59.3, H 4.8, Cl 11.9, N 13.9%.

EXAMPLE 48

5.0 g (24.8 millimoles) of 2-(p-aminophenyl)-3,4-diaza-bicyclo[4.1.0]hept-2-en-5-one, 5.2 g (30.0 millimoles) of 2,2-dichlorocyclopropanecarboxylic acid chloride and 100 ml of absolute tetrahydrofuran are refluxed for 6 hours. The product is filtered off at 10° C., washed with water and recrystallized from a dimethylformamide/water mixture. 4.1 g (49% of theory) of 2-[p-(2,2-dichlorocyclopropylcarbonylamino)-phenyl]-3,4-diaza-bicyclo[4.1.0]hept-2-en-5-one are obtained as colorless crystals, of melting point 264°–265° C.

Analysis for $C_{15}H_{13}Cl_2N_3O_2$: calculated: C 53.3, H 3.9, Cl 21.0, N 12.4%: found: C 52.9, H 3.9, Cl 20.8, N 12.5%.

The following are examples of formulations which are prepared in a conventional manner:

| 1. Tablets: | |
|---|---|
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10 percent strength aqueous solution of polyvinylpyrrolidine, forced through a sieve of 1.0 mm mesh size and dried at 50° C. The granules obtained are mixed with polyethylene glycol (mean molecular weight 4,000), hydroxypropylmethylcellulose, talc and magnesium stearate and the mixture is molded to give tablets each weighing 240 mg.

| 2. Example of dragees: | |
|---|---|
| Active compound | 10 mg |
| Lactose | 90 mg |
| Corn Starch | 60 mg |
| Polyvinylpyrrolidone | 6 mg |
| Magnesium stearate | 1 mg |
| | 167 mg |

A mixture of the active compound with the lactose and the corn starch is moistened with an 8 percent strength aqueous solution of the polyvinylpyrrolidone, granulated by forcing through a 1.5 mm sieve, dried at 50° C. and forced through a 1.0 mm sieve. The granules thus obtained are mixed with magnesium stearate and the mixture is molded to give dragee cores. These are then coated in a conventional manner with a shell essentially consisting of sugar and talc.

We claim:

1. A 2-aryl-3,4-diaza-bicyclo[4.1.0]hept-2-en-5-one of the formula I

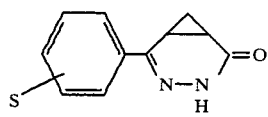 (I)

where S is p-alkyl of 1 to 4 carbon atoms, p-cycloalkyl of 4 to 6 carbon atoms in the ring, p-alkoxy of 1 to 3 carbon atoms, p-phenyl, p-halogen, p- or m-amino, m-nitro, p- or m-cyano, p- or m-(pyrrol-1-yl) or p- or m-acylamino of the formula —NHCOR$^1$, where R$^1$ is hydrogen, alkyl of 1 to 8 carbon atoms, which is unsubstituted or substituted by from one to six halogen atoms, cycloalkyl of 3 to 8 carbon atoms in the ring, which is unsubstituted or substituted by from one to four halogen atoms and/or alkyl radicals of 1 to 4 carbon atoms, alkenyl of 2 to 8 carbon atoms or phenyl which is unsubstituted or substituted by alkyl of 1 to 3 carbon atoms, by alkoxy of 1 to 3 carbon atoms or by a halogen atom.

2. A compound of the formula I, where S is a p-acylamino group of the formula —NHCOR$^1$, where R$^1$ is alkyl of 1 to 4 carbon atoms which is unsubstituted or substituted by from one to three halogen atoms, or is cycloalkyl of 3 to 5 carbon atoms in the ring, which is unsubstituted or substituted by from one to three halogen atoms and/or methyl radicals, or is alkenyl of 2 to 4 carbon atoms.

3. 2-(p-Acetylaminophenyl)-3,4-diaza-bicyclo[4.1.0]hept-2-en-5-one.

4. 2-(p-Propionylaminophenyl)-3,4-diaza-bicyclo-[4.1.0]hept-2-en-5-one.

5. 2-(p-Chloroacetylaminophenyl)-3,4-diaza-bicyclo-[4.1.0]hept-2-en-5-one.

6. 2-[p-(2-Chloropropionylamino)-phenyl]-3,4-diaza-bicyclo[4.1.0]hept-2-en-5-one.

7. 2-(p-Cyclopropylcarbonylaminophenyl)-3,4-diaza-bicyclo[4.1.0]hept-2-en-5-one.

8. 2-(p-Cyclobutylcarbonylaminophenyl)-3,4-diaza-bicyclo[4.1.0]hept-2-en-5-one.

9. 2-(p-Acryloylaminophenyl)-3,4-diaza-bicyclo-[4.1.0]hept-2-en-5-one.

10. A therapeutic agent for reducing hypertension and inhibiting thrombocyte aggregation in mammals which consists essentially of a pharmaceutically acceptable carrier or diluent and as an active compound an effective amount of a compound set forth in claim 1.

11. A therapeutic agent as set forth in claim 10 wherein the active compound is 2-[p-(2-chloropropionylamino)-phenyl]-3,4-diaza-bicyclo[4.1.0]hept-2-en-5-one.

12. A therapeutic agent as set forth in claim 10 wherein the active compound is 2-(p-cyclopropylcarbonylaminophenyl)-3,4-diaza-bicyclo[4.1.0]hept-2-en-5-one.

13. A therapeutic agent as set forth in claim 10 wherein the active compound is 2-(p-cyclobutylcarbonylaminophenyl)-3,4-diaza-bicyclo-[4.1.0]hept-2-en-5-one.

14. A therapeutic agent as set forth in claim 10 wherein the active compound is 2-(p-acryloylaminophenyl)-3,4-diaza-bicyclo[4.1.0]-hept-2-en-5-one.

15. A therapeutic agent as set forth in claim 10 wherein the active compound is 2-(p-acetylaminophenyl)-3,4-diaza-bicyclo[4.1.0]hept-2-en-5-one.

16. A therapeutic agent as set forth in claim 10 wherein the active compound is 2-(p-propionylaminophenyl)-3,4-diaza-bicyclo[4.1.0]-hept-2-en-5-one.

17. A therapeutic agent as set forth in claim 10 wherein the active compound is 2-(p-chloroacetylaminophenyl)-3,4-diaza-bicyclo-8 4.1.0]hept-2-en-5-one.

* * * * *